(12) United States Patent
Schmiedl et al.

(10) Patent No.: US 9,849,005 B2
(45) Date of Patent: Dec. 26, 2017

(54) IMPLANT AND METHOD FOR MANUFACTURING SAME

(71) Applicant: BIOTRONIK AG, Beulach (CH)

(72) Inventors: Robert Schmiedl, Hirschaid (DE);
Matthias Gratz, Erlangen (DE); Max Schaldach, Berlin (DE); Volker Lang, Berlin (DE)

(73) Assignee: Biotronik AG, Buelach (CH)

( * ) Notice: Subject to any disclaimer, the term of this patent is extended or adjusted under 35 U.S.C. 154(b) by 397 days.

(21) Appl. No.: 13/858,696

(22) Filed: Apr. 8, 2013

(65) Prior Publication Data

US 2013/0274869 A1 Oct. 17, 2013

Related U.S. Application Data

(60) Provisional application No. 61/624,403, filed on Apr. 16, 2012.

(51) Int. Cl.
*A61F 2/82* (2013.01)
*A61L 31/10* (2006.01)
*A61L 31/14* (2006.01)

(52) U.S. Cl.
CPC .......... *A61F 2/82* (2013.01); *A61L 31/10* (2013.01); *A61L 31/148* (2013.01)

(58) Field of Classification Search
CPC ........ A61L 2300/622; A61L 2300/608; A61M 37/0092; A61N 2007/0039; A61F 2250/0067; A61F 2250/0068; A61F 2250/0071; A61F 2310/0097; A61F 2002/30677
See application file for complete search history.

(56) References Cited

U.S. PATENT DOCUMENTS

| 6,287,285 | B1* | 9/2001 | Michal | A61L 31/10 424/422 |
| 6,344,209 | B1* | 2/2002 | Saito | A61K 47/26 424/426 |
| 6,896,659 | B2* | 5/2005 | Conston | A61B 8/481 600/458 |
| 2002/0082679 | A1* | 6/2002 | Sirhan | A61F 2/91 623/1.15 |
| 2003/0153981 | A1* | 8/2003 | Wang | A61F 2/30767 623/22.21 |
| 2003/0230819 | A1* | 12/2003 | Park | A61L 31/16 264/4 |

(Continued)

FOREIGN PATENT DOCUMENTS

WO 2012148265 A1 11/2012

OTHER PUBLICATIONS

EP13162943.8 European Search Report dated Sep. 22, 2015.

*Primary Examiner* — Jacqueline Woznicki
(74) *Attorney, Agent, or Firm* — Wagenknecht IP Law Group PC

(57) ABSTRACT

A method for manufacturing an implant and an implant, in particular an intraluminal endoprosthesis, including a body having a coating on at least a portion of the surface thereof, and the degradation of which can be influenced from the outside in a targeted manner, the method having the following steps:
a) providing an implant body, and
b) applying a coating to the surface of the implant body, wherein the coating comprises unfilled cavities, preferably in the form of microbubbles (2).

7 Claims, 3 Drawing Sheets

(56) References Cited

U.S. PATENT DOCUMENTS

| | | |
|---|---|---|
| 2004/0077948 A1 | 4/2004 | Violante et al. |
| 2005/0074406 A1 | 4/2005 | Couvillon, Jr. et al. |
| 2006/0093646 A1* | 5/2006 | Cima .................. A61C 8/0012 |
| | | 424/425 |
| 2006/0171989 A1* | 8/2006 | Prescott ............... A61K 9/0024 |
| | | 424/426 |
| 2008/0181853 A1* | 7/2008 | Ottoboni ................ A61B 8/481 |
| | | 424/9.52 |
| 2009/0123517 A1* | 5/2009 | Flanagan .................. A61F 2/91 |
| | | 424/423 |
| 2009/0299468 A1* | 12/2009 | Schewe ................ A61L 31/082 |
| | | 623/1.46 |
| 2009/0304775 A1* | 12/2009 | Joshi .......................... A61F 2/30 |
| | | 424/426 |
| 2012/0046734 A1* | 2/2012 | Girton .................. A61L 31/146 |
| | | 623/1.42 |

\* cited by examiner

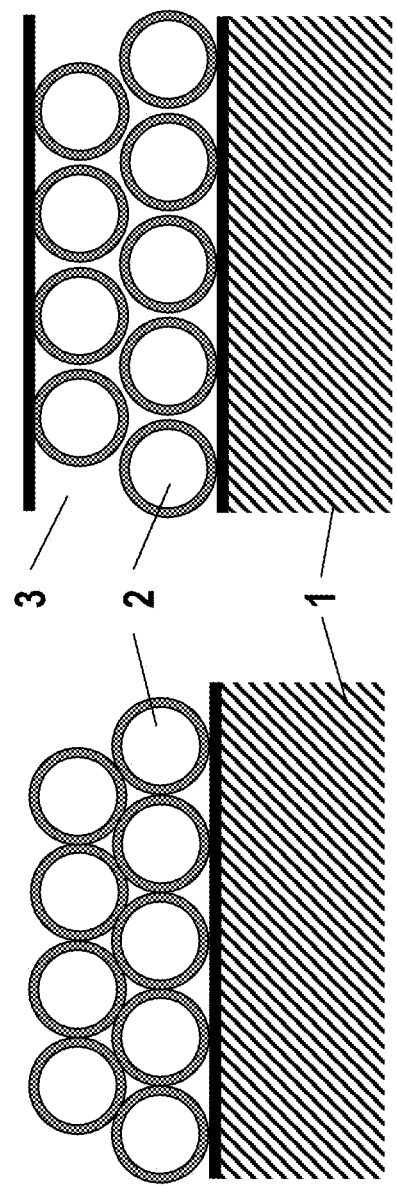

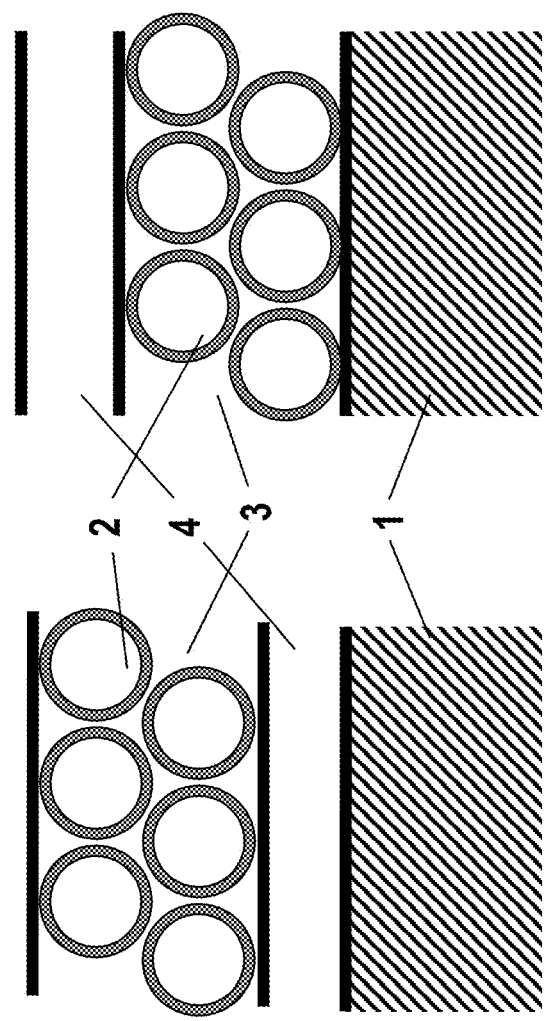

IMPLANT AND METHOD FOR MANUFACTURING SAME

CROSS REFERENCE TO RELATED APPLICATIONS

This application claims benefit of priority to US provisional patent application Ser. No. 61/624,403 filed Apr. 16, 2012; the content of which is herein incorporated by reference in its entirety.

TECHNICAL FIELD

The invention relates to a method for manufacturing an implant, in particular an intraluminal endoprosthesis, including a body having a coating on at least a portion of the surface thereof, and a corresponding implant.

BACKGROUND

A wide variety of medical endoprostheses or implants for highly diverse applications are known from the prior art. Within the scope of the present invention, implants are understood to be endovascular prostheses or other endoprostheses, such as stents, fastening elements for bone, such as screws, plates, or nails, surgical suture material, intestinal clamps, vascular clips, prostheses in the area of hard and soft tissue, and anchoring elements for electrodes, in particular of pacemakers or defibrillators.

Today, stents that are used to treat stenoses (vascular constrictions) are used particularly frequently as implants. They include a body in the form of a tubular or hollow cylindrical matrix lattice that is open at both longitudinal ends. The tubular matrix lattice of an endoprosthesis of this type is inserted into the vessel to be treated, and is used to support the vessel. Stents have become established for use to treat vascular diseases in particular. The use of stents enables constricted regions in the vessels to be expanded, thereby increasing the lumen. Although the use of stents or other implants makes it possible to obtain an optimal vascular cross section that is necessary primarily for therapeutic success, the permanent presence of a foreign body of that type initiates a cascade of microbiological processes that can result in gradual closure of the stent and, in the worst case, to vascular occlusion.

SUMMARY

A starting point for solving this problem is to produce the stent or other implants out of a degradable or biodegradable material.

Degradation generally refers to hydrolytic or oxidative degradative processes, including metal-catalyzed oxidation, while biodegradation refers to hydrolytic, enzymatic and other degradative processes in the living organism, which are caused primarily by the bodily fluids that come in contact with the biodegradable material and result in a gradual disintegration of the structures of the implant that contain the biodegradable material. Due to this process, the implant loses its mechanical integrity at a certain point in time. The term "biocorrosion" is often used as a synonym for the term "biodegradation". The term "bioresorption" includes the subsequent resorption of the degradative products by the living organism.

Stents that comprise coatings having various functions are already known. Such coatings are used, for instance, to release drugs, to place an x-ray marker or to protect the underlying structures. Moreover, coatings are used to control degradation, such as to delay degradation.

When creating biodegradable implants, the degradability should be controlled according to the desired therapy or the use of the particular implant (coronary, intracranial, renal, etc.). For many therapeutic applications it is desirable for the implant to lose its integrity or start to lose its integrity at a certain point in time or time period that can be specified from the outside. In this case integrity, that is, mechanical integrity, refers to the property that the implant has practically no mechanical deterioration compared to the undegraded implant. This means that the implant is still so mechanically stable that the collapse pressure, for example, has decreased only slightly, i.e. to 80% of the nominal value at the most. The implant can therefore still perform the main function thereof, which is to hold the vessel open, provided integrity exists. Alternatively, integrity can be defined as the implant being so mechanically stable that it undergoes hardly any geometric changes in the loaded state thereof in the vessel, for example, it does not collapse or break to a noticeable extent, it has at least 80% of the dilatation diameter under load, or in the case of a stent, hardly any of the supporting struts have begun to break.

Different mechanisms for controlling the degradation of implants have already been described in the prior art. These are based, for example, on anorganic and organic protective layers or the combination thereof that withstand the corrosive environment in the treated organism and the corrosion processes taking place there. Solutions known so far are characterized in that barrier layer effects are attained that are based on a spatial separation of the corrosion medium from the material of the implant body with the fewest possible defects. The result is that degradation time is extended. For example, degradation protection is secured by way of various combined protective layers and defined geometric separations (diffusion barriers) between the corrosion medium and the implant body material. Other solutions are based on changing alloy components of the biodegradable material of the implant body in a targeted manner. However, the aforementioned solutions do not make it possible to place the disintegration caused by the degradation process and the resulting strut breakage in a time window that is variable but can be matched to a certain treatment success, for example, from the outside. Degradation in implants often starts too soon or too late, or the duration of the degradation of the implant is too undetermined.

A further problem associated with coatings and degradation control results because stents or other implants typically assume two states, namely a compressed state having a small diameter and an expanded state having a larger diameter. In the compressed state, the implant can be introduced using a catheter into the vessel to be supported, and can be positioned at the point to be treated. At the treatment site, the implant is then dilated using a balloon catheter, for example. Due to this change in diameter, the body of the implant is subjected to a strong mechanical load. Further mechanical loading of the implant can occur during production or if the implant moves in or with the vessel into which the implant has been inserted. The above-mentioned coatings therefore result in the disadvantage that they tear (e.g. micro-fissures form) or are partially removed during deformation of the implant. As a result, local degradation can be induced at a point in time at which degradation is not yet desired. In addition, the onset and rate of degradation are dependent on the size and distribution of micro-fissures produced by the deformation, which are flaws that are difficult to control. This results in strong scattering of the degradation times.

The problem addressed by the present invention is therefore that of creating an implant that makes it possible for the implant to safely degrade within a variable time window that can be specified from the outside. Accordingly, another problem addressed by the invention is that of providing a simple method for manufacturing such an implant.

The statement of the problem mentioned above is solved by a method having the following steps:
a) provide the implant body,
b) apply the coating to the surface of the implant body, wherein the coating comprises unfilled cavities, preferably in the form of microbubbles.

The advantage of the depicted method is that an implant can be manufactured using a simple procedure, wherein the implant makes it possible to control degradation from the outside of the body (extracorporeal degradation control) in a specified manner. The unfilled cavities and, optionally, additional filled cavities first protect the surface of the implant body and prevent or minimize degradation.

Within the scope of the present invention, the term "unfilled cavities" refers to cavities or vessicles that contain a gas in the cavity but are not filled with a fluid or a solid. By contrast, "filled cavities" refers to cavities that have a solid and/or a fluid in the interior thereof.

The present invention is based on the finding in particular that gas-filled cavities are compressible and can therefore be useful within the scope of the present invention. (This does not apply for vessicles filled with fluid or solids.) Due to the compressibility, unfilled cavities can be induced to oscillate using ultrasound at any point in time from a location outside of the treated organism, for example when it has been determined that healing has progressed to a sufficient extent. If the amplitude is sufficient, the mechanical deformation of the walls of the cavities caused by oscillations induced by external intervention causes the walls to rupture or tear, thereby destroying the covering of the cavities. The ultrasound amplitude required to excite the oscillation is that much lower the closer the frequency of the excitation oscillation comes to the resonance frequency of the system to be excited. When excited with the resonance frequency, the cavities begin to oscillate before all the other objects in the surroundings.

Due to the destruction of the covering (walls) of the cavities, degradation of the coating is accelerated because parts of the coating are removed as a result. Moreover, the fluid present in the organ to be treated can be more easily accessed at deeper points of the implant, and therefore degradation progresses there as well. The destruction of the coating can go so far that the surface of the implant body is at least partially exposed, thereby causing it to degrade immediately.

The body of the implant includes at least one part of the implant, preferably the main part of the implant, that is responsible for the mechanical integrity of the implant. In the present invention, the implant body preferably contains a material or a plurality of materials from the group containing biodegradable metals such as magnesium, iron, biodegradable alloys comprising the elements magnesium, iron, zinc, molybdenum and/or tungsten, biodegradable polymers, for example, polylactides, poly(lactide-co-glycolide), polyhydroxyalkanoates, caprolactone, or the implant body is made of a material or a plurality of materials from this group.

In a preferred embodiment, the cavities are formed by microbubbles, which are also referred to as bubbles. Microbubbles have a flexible covering or shell, while microcapsules have a rigid shell. The advantage of using microbubbles is that the covering thereof is capable of resonant oscillation due to the flexibility thereof and can therefore be excited to oscillate and can be destroyed particularly efficiently using ultrasound. For a coating comprising microbubbles according to the invention, there is only a narrow frequency range in which—given a fixed excitation amplitude—the amplitude response of the unfilled bubbles increases to a multiple of the value thereof at lower or higher frequencies. A characteristic of the property of suitable microbubbles is an at least two-fold resonance step-up, preferably at least three-fold, more preferably an at least five-fold resonance step-up in the aforementioned narrow frequency range compared to the frequencies used within the scope of a diagnostic application of ultrasound, for example.

In the present invention, unfilled cavities contain air or nitrogen, for example. Preferably, a gas can be used as the filling medium that has large molecules, which are incapable of diffusing through the wall of the cavity into the surrounding bodily fluid (e.g. blood), and/or which are poorly soluble in blood, such as perfluorocarbons (e.g. perfluorobutane n-$C_4F_{10}$) or $SF_6$.

In one embodiment, filled cavities, which are provided in addition, comprise a liquid or solid material instead as the filling, for example a liquid or solid pharmaceutically active substance and/or a diagnostic substance.

Moreover, it is advantageous with respect to the present invention that the ultrasound excitation used for degradation simultaneously increases the efficiency of the uptake of active agent into the cells of the target tissue of the treatment, for example into the cells of a blood vessel. After implantation, the cavities, which can be ruptured by way of ultrasonic excitation, are located in the immediate vicinity of the cells of the target tissue. The destruction of the cavities by ultrasound also has the effect of sonoporation in the target tissue due to the spatial vicinity to the target tissue. As a result, molecules of a pharmaceutically active substance can enter the cells of the target tissue not only by way of the transport mechanisms of an intact cell wall, but also directly through the temporarily created pores in the target tissues as the take-up path into the cells.

It has also proven advantageous that the flexible structure of the coating has a high plastic deformation capability, in particular when microbubbles are used. As a result, the integrity of the coating is retained even during processing and implantation of the stent. The coating therefore does not undergo delamination to a notable extent before the coating is destroyed in a targeted manner.

The preferred range of the resonance frequency, which is between 0.2 MHz and 10 MHz, is specific for each implant type and depends on the intended application site thereof and, in fact, on the fundamental condition that the range of the ultrasound in this frequency range must be so great that, at the depth of the implant site below the surface of the body, the required sound intensity is still achieved that is sufficient to excite the walls of the cavities to oscillate in such a way that they tear or rupture. For coronary implants, for example, the implantation depth is approximately 10 cm to 20 cm, and therefore the preferred resonance range is in the frequency range between 0.2 MHz and 2 MHz, further preferably between 0.2 MHz and 1 MHz. Higher frequencies are possible for peripheral vascular supports in the leg or neck region at depths of a few centimeters, and are preferably between 1 MHz and 10 MHz, particularly preferably between 2 MHz and 5 MHz. Resonance frequencies in the determined range can be achieved by suitably selecting the material, the thickness of the wall and the mean size of the cavities. The resonance frequency that is definitive for the application is a function of the cavity diameter, the chemical composition of the walls of the cavities, and the characteristic of the interactions between the cavities in the coatings according to the invention. The mean cavity diameter is preferably in the range of 50 nm to 25 µm, particularly preferably in the range of 50 nm to 5 µm.

Within the scope of the present invention, the resonance frequency refers to the frequency at which the entire system of cavities in the aqueous environment or in the surroundings of the bodily fluid has resonance. A 0.9% saline solution, for example, can be used as a test environment for this purpose.

To prevent the coating from wearing off as the implant is guided to the site of the treatment in the body of the treated organism, the coating can be preferably disposed in protected parts of the carrying structure of the implant body, preferably on the luminal side of the implant body and/or in recesses (grooves) and/or in indentations and/or in hole-like openings in the implant body. The coating comprising the cavities, preferably the microbubbles, is preferably applied using an aqueous suspension. Other solvents can be used if necessary, such as dimethyl sulfoxide (DMSO).

In a further embodiment of the implant according to the invention, it comprises a coating having a first layer having only unfilled cavities, and a second layer containing at least one pharmaceutically active substance and/or at least one diagnostic substance, wherein either the first layer is applied to the surface of the implant body first and then the second layer is applied onto the surface of the first layer, or the coating is carried out in the reverse order. The advantage of the first variant of the layer structure having a first layer disposed underneath the second layer is that delivery of an active agent from the second layer is not influenced by the properties of the first layer, with respect to diffusion, for example. The advantage of the second variant of the layer structure, in which the first layer is disposed above the second layer, is that the delivery of active agent from the second layer can be controlled by way of the destruction of the cavity layer (first layer), preferably by way of the above-described excitation using an ultrasound source from a site outside of the body.

A "pharmaceutically active substance" (or therapeutically active or effective substance) is understood to mean, within the scope of the invention, a plant-based, animal-based, or synthetic active agent (drug) or a hormone that is used in suitable doses as a therapeutic agent to influence states or functions of the body, as a replacement for active agents that are produced naturally by human or animal bodies, such as insulin, and to eliminate or render harmless pathogens, tumors, cancer cells, or foreign substances. The release of the substance into the surroundings of the implant has a positive effect on the healing process or counteracts pathological changes in the tissue after a surgical procedure, or serves to render diseased cells harmless in oncology.

Pharmaceutically active substances of that type typically have e.g. an antiinflammatory and/or antiproliferative and/or spasmolytic effect, thereby making it possible to prevent e.g. restenoses, inflammation, or (vascular) spasms. Substances of that type can be composed, for example, of one or more substances from the active ingredient group of calcium channel blockers, lipid regulators (e.g. fibrates), immunosuppressants, calcineurin inhibitors (e.g. Tacrolimus), antiphlogistics (e.g. cortisone or dichlofenac), anti-inflammatory drugs (e.g. imidazole), antiallergenics, oligonucleotides (e.g. dODN), estrogens (e.g. genistein), endothelium formers (e.g. fibrin), steroids, proteins, hormones, insulins, cytostatic agents, peptides, vasodilators (e.g. Sartane) and the anti-proliferative substances of taxols or taxanes, preferably in this case paclitaxel or sirolimus and derivatives (rapalogues), and the epothilones. Further pharmaceutically active substances include immunmodulators, statins, cardiovascular active agents, nucleic acids such as plasmids, siRNA, miRNA and dsRNA.

Diagnostic substances within the scope of the invention include, mutatis mutandis, contrast medium for x-ray or MR diagnostics (e.g. rare earths) and specific substances for the specific marking of certain endogenous structures, including certain cell types, cellular components, messenger substances and/or biomarkers.

The degradation of the coating and, therefore, the implant can be controlled even better when the shell of the cavities contains biodegradable materials, preferably at least one material from the group containing lipids, phospholipids, polysaccharides, proteins, peptides, collagens, elastins, fibrins, chitosans, hyaluronic acids, chondroitin sulfates, hydro gels and synthetic polymers, such as PLA, polyamide esters, polyvinyl esters, polyvinyl alcohols.

Biodegradable materials that are suitable for the implant body or the coating can contain polymers or metals, for example. The body or the coating can be made of a plurality of the materials. Examples of suitable polymeric compounds are polymers of the group cellulose, collagen, albumin, casein, polysaccharide (PSAC), polylactic acid (PLA), poly-L-lactide (PLLA), polyglycol (PGA), poly(D,L-lactide-co-glycolide) (PDLLA-PGA), polyhydroxybutyric acid (PHB), polyhydroxy valeric acid (PHV), poly(alkyl carbonate), poly (orthoester), polyethylenterephtalat (PET), polymalonic acid (PML), polyanhydrides, polyphosphazenes, polyamino acids and their copolymers, and hyaluronic acid. Depending on the properties that are desired, the polymers can be present in pure form, in derivatized form, in the form of blends, or as copolymers.

If cavities are used in the form of microcapsules or microbubbles, they can attached to the surface of the implant body using an embedding matrix containing at least one material from the group comprising polymers, lipids, softening agents based on citrate (e.g. BTHC (n-Butyryl-tri-n-hexyl citrate)), proteins and peptides and/or using a primer and/or using active groups disposed on the surface of the microbubbles or microcapsules. Further alternatives or additional possibilities for attaching the microbubbles or microcapsules to the surface of the implant body include attaining a form-fit connection in the union due to chemical interactions of the components of the embedding matrix, e.g. proteins, or due to chemical interaction of the wall components of the cavities, preferably proteins, peptides or substances having analogous chemical properties. In one embodiment, the matrix material can also comprise a pharmaceutically active substance and/or a diagnostic substance.

The coating having the cavities, preferably the microbubbles, is produced by way of immersion, pipetting or spraying, preferably as aqueous suspension, followed by drying, if necessary. Before, during or after the cavities— preferably the microbubbles—are applied, as an aqueous suspension, for example, the embedding matrix can be applied to the appropriate regions of the implant body, possibly in an aqueous solution containing at least one material from the group consisting of polymers, lipids, citrate-based softening agents, proteins and peptides and/or a primer, preferably likewise by way of immersion, pipetting or spraying.

If desired, a further layer, a polymeric layer, for example, can be applied to the coating having the cavities, as corrosion protection in order to minimize degradation before the ultrasound-activated destruction of the walls of the cavities, or to increase the gliding quality of the coating. Suitable materials of the further layer are preferably the above-mentioned biodegradable polymers. The irregular structure of the coating results in good adhesion of the further layer on the coating.

The above-noted statement of the problem is further solved by an implant that can be or is produced using one of the above-described methods according to the invention. Such an implant has the advantages mentioned above in conjunction with the manufacturing method according to the invention.

The method according to the invention and the implant according to the invention are explained in the following in examples with reference to figures. All of the features described and/or depicted graphically form the subject matter of the invention, also independently of their combination in the claims or their back-references.

DESCRIPTION OF THE DRAWINGS

Shown schematically, in a cross section in each case, are:
FIG. 1 a first example embodiment of an implant according to the invention,
FIG. 2 a second example embodiment of an implant according to the invention,
FIG. 3 a third example embodiment of an implant according to the invention,
FIG. 4 a fourth example embodiment of an implant according to the invention and
FIG. 5 a fifth example embodiment of an implant according to the invention.

DETAILED DESCRIPTION

Figure 5:
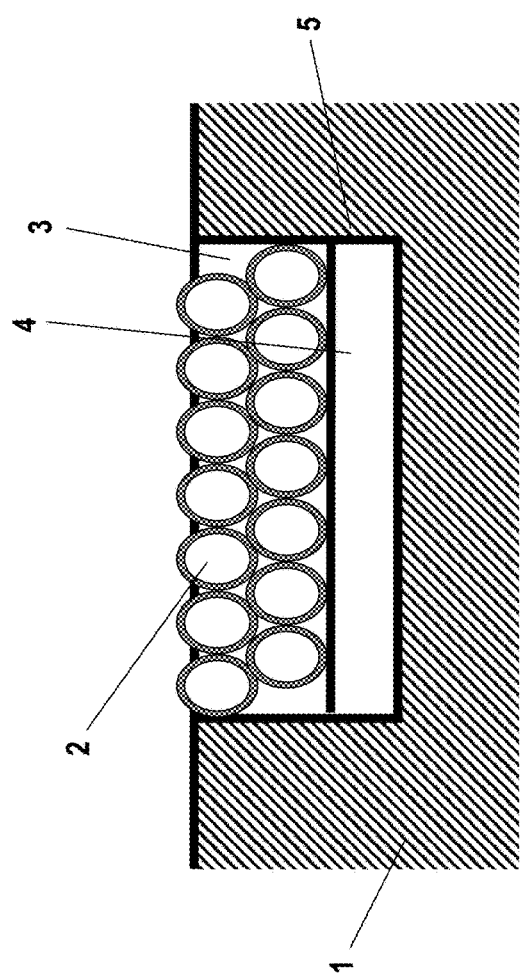

FIG. 1 shows a section of a stent, namely the section of a stent strut 1 made of a magnesium alloy comprising at least 50% magnesium by weight. A coating including microbubbles 2 made of PLA is disposed on the outer surface of the stent strut 1. The inner space of the microbubbles 2 is filled with an inert, poorly soluble gas, such as nitrogen or sulphur tetrachloride ($SF_6$). The mean diameter of the microbubbles 2 is approximately 5 μm. The microbubbles 2 are attached by way of the surface tension thereof to the outer surface of the stent strut 1 and, additionally, chemical anchor chains can be applied onto/into the wall of the microbubbles 2 to improve the adhesion of the microbubbles 2 to the surface of the stent strut 1.

The second example embodiment, which is presented in FIG. 2, corresponds to the example shown in FIG. 1, with the difference that the microbubbles 2 are embedded in a matrix 3 made of PLLA or hyaluronic acid.

Example embodiments of an implant according to the invention are presented in FIGS. 3 and 4, which correspond to the second example embodiment and additionally include a layer 4 having a pharmaceutically active substance, wherein the layer 4 contains BTHC and paclitaxel, for example, in the case of FIG. 3, and PLLA and sirolimus, for example, in the case of FIG. 4. In the third example embodiment, which is shown in FIG. 3, the layer 4 is disposed underneath the layer comprising the microbubbles 2, while, in the example embodiment depicted in FIG. 4, the layer 4 having the pharmaceutically active substance lies above the layer having the microbubbles 2. Analogous to the second example embodiment, all the microbubbles 2 are embedded in the matrix 3. Alternatively, and analogous to the first example embodiment depicted in FIG. 1, the microbubbles can also be attached to the surface of the stent strut 1 or the layer 4 without matrix material.

Finally, FIG. 5 shows an example embodiment, in the case of which a layer 4 including hyaluronic acid and an anti-inflammatory agent is disposed in a recess 5 in the stent strut 1. A further layer is disposed over the layer 4, likewise in the recess 5, the layer including microbubbles 2 made of PLA with a matrix 3 made of PLLA or hyaluronic acid, which is disposed on the surface of the layer 4 and within the recess 5. Alternatively, the microbubbles 2 can be disposed on the layer 4 in the recess 5 by way of the surface tension thereof, or by way of a form-fit connection in the recess 5, i.e. without a matrix.

The production of an implant according to the invention is presented in the following using the example of a biodegradable vascular support in the form of a coronary stent.

The support frame of the vascular support is a biodegradable, balloon-expandable metal stent, produced by way of laser cutting from a tube made of the biocompatible, biodegradable magnesium alloy WE43. The stent is provided with recesses at a plurality of defined points for accommodating microbubbles. The recesses can also be produced by way of laser cutting. The recesses are preferably disposed in strut regions that, during dilation, undergo less mechanical load or are hardly deformed at all compared to other regions.

To facilitate a coating to be applied into the recesses in a targeted manner, the stent is mounted on a positioning device in a micropipetting system.

Immediately before coating, a microbubble suspension of microbubbles having a size of 2 μm to 10 μm and comprising a phospholipid shell containing the filling gas $SF_6$ is prepared. The suspension is preferably reconstituted from the granulate (e.g. SONOVUE from BRACCO Imaging S.p.A., Amsterdam), well sealed from the air, with addition of an aqueous solvent, for example a 0.9% saline solution (optionally with additives), and intensive shaking for a period of at least 20 s until a homogeneous, milky white suspension is obtained. The suspension produced in this manner is filled into the micropipetting system and is applied onto/into the above-mentioned recesses or other protected regions on the support frame. The deposited droplets of the suspension containing the microbubbles remain adhered in the recesses by way of the surface tension thereof. In a preferred example embodiment, the suspension is propelled in the micropipetting system by application of pressure with the filling gas $SF_6$. This gas also serves to prevent other gasses from entering.

Alternatively or in addition to phospholipids, the microbubble shells can contain at least one material from the group comprising galactose, albumin and Perflutren.

In the next step, the matrix component, which in this case is hyaluronic acid in aqueous solution, is added to the layer comprising the microbubbles, which is disposed in the recesses, in the same manner using the micropipetting system. The matrix component serves to adhere the microbubbles onto the surface of the stent. Application in a subsequent manner permits the matrix component to come to rest primarily in the outer regions of the coating and to thereby better protect the more deeply embedded bubbles against damage.

Alternatively, the matrix component of the layer, which in this case is hyaluronic acid in aqueous solution, can be applied into the recesses using the micropipetting system together (i.e. simultaneously) with the microbubble suspension. To this end, the two solutions are combined immediately before emerging from the outlet opening of the micropipetting system from separate reservoirs. The matrix component becomes evenly distributed in the coating, thereby resulting in uniform acoustic properties of the embedded microbubbles. By shutting off the driving pumps at different times, it is possible for the matrix component to be disposed primarily in the outer regions of the coating, thereby protecting the more deeply embedded microbubbles against damage.

Finally, in both variants of the application, an (incomplete/partial) drying step is carried out, which serves the primary purpose of stabilizing the outer surface of the bubble depots disposed in the recesses for the subsequent processing steps. To this end, the coated stent support frame is stored in a dry environment, e.g. in a slow (laminar) stream of cold or moderately heated nitrogen or argon or another inert gas, e.g. at a temperature in the range of 10° C. to 50° C., for a specific time period of a few minutes.

For drying, an alternative to the use of the slow stream is to use a closed drying room with removal of water by way of at least one cooling finger (cooled with liquid nitrogen, dry ice or Peltier cooling) or a constant-temperature oven with a stationary inert-gas atmosphere.

Finally, a coating containing PLLA is applied to the stent, over the entire surface or only a portion thereof, by way of spray coating. The PLLA coating provides protection against corrosion for the corresponding regions of the stent, improves the mechanical adhesion of the microbubble layer and protects it against wear.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS

1 Stent strut
2 Microbubble
3 Matrix
4 Layer comprising pharmaceutically active substance
5 Recess

What is claimed is:

1. A method for manufacturing a biodegradable implant comprising the following steps:

a) providing an implant body;

b) applying a pharmaceutical layer to the implant body, wherein the pharmaceutical layer comprises a pharmaceutically active substance; and c) applying a coating comprising rupturable, unfilled microbubbles over the pharmaceutical layer, wherein the microbubbles are configured to rupture by way of ultrasonic excitation.

2. The method according to claim 1, wherein the microbubbles are formed of polylactic acid (PLA) and the pharmaceutically active substance is hyaluronic acid.

3. A biodegradable implant comprising a body at least partially coated with a pharmaceutical layer and over the pharmaceutical layer is a coating of microbubbles filled with inert gas and configured to rupture by way of ultrasonic excitation.

4. The implant according to claim 3, characterized in that the implant body comprises struts, wherein a luminal side of the struts comprises recesses coated with the microbubbles.

5. A biodegradable implant comprising a body at least partially coated with a pharmaceutical layer coated with microbubbles filled with inert gas and configured to rupture by way of ultrasonic excitation, characterized in that the microbubbles are attached to a surface of the implant body using an embedding matrix, wherein the matrix comprises at least one material selected from the group consisting of a polymer, a lipid, a citrate-based softening agent, a protein and a peptide.

6. The implant according to claim 3, wherein the gas comprises molecules sized to prevent diffusion of the molecules through shells of the microbubbles.

7. The implant according to claim 3, wherein the gas comprises perfluorocarbons or sulphur tetrafluoride.

* * * * *